United States Patent [19]

Breu

[11] Patent Number: 5,023,916

[45] Date of Patent: Jun. 11, 1991

[54] METHOD FOR INSPECTING THE LEADS OF ELECTRICAL COMPONENTS ON SURFACE MOUNT PRINTED CIRCUIT BOARDS

[75] Inventor: Heinz Breu, Mountain View, Calif.

[73] Assignee: Hewlett-Packard Company, Palo Alto, Calif.

[21] Appl. No.: 399,688

[22] Filed: Aug. 28, 1989

[51] Int. Cl.[5] ............................................. G06K 9/00
[52] U.S. Cl. ....................................... 382/8; 356/237; 358/106
[58] Field of Search ...................... 382/8, 54; 356/237; 358/106

[56] References Cited

U.S. PATENT DOCUMENTS

| 4,688,939 | 8/1987 | Ray | 358/106 |
| 4,772,125 | 9/1988 | Yoshimura et al. | 358/106 |
| 4,802,231 | 1/1989 | Davis | 382/57 |
| 4,827,533 | 5/1989 | Tanaka | 382/54 |

OTHER PUBLICATIONS

Young & Fu, "Dynamic Programming Methods," *Handbook of Pattern Eec. and Image Processing* (Academic Press, 1986) pp. 501–509.

*Primary Examiner*—Leo H. Boudreau
*Assistant Examiner*—David Fox

[57] ABSTRACT

A method of inspecting solder joints that connect surface-mount electronic components to printed circuit boards is provided. Preferably, the method includes the steps of obtaining an image of a plurality of the leads of the electronic component, for each obtained image, representing segments of the image that correspond to each of the leads by polygons, projecting pixel intensity values within each polygon each onto an axial dimension to provide a measured waveform, comparing the measured waveform for each lead with a corresponding model waveform, and, classifying each lead as being either satisfactory or unsatisfactory on the basis of said comparisons.

5 Claims, 5 Drawing Sheets

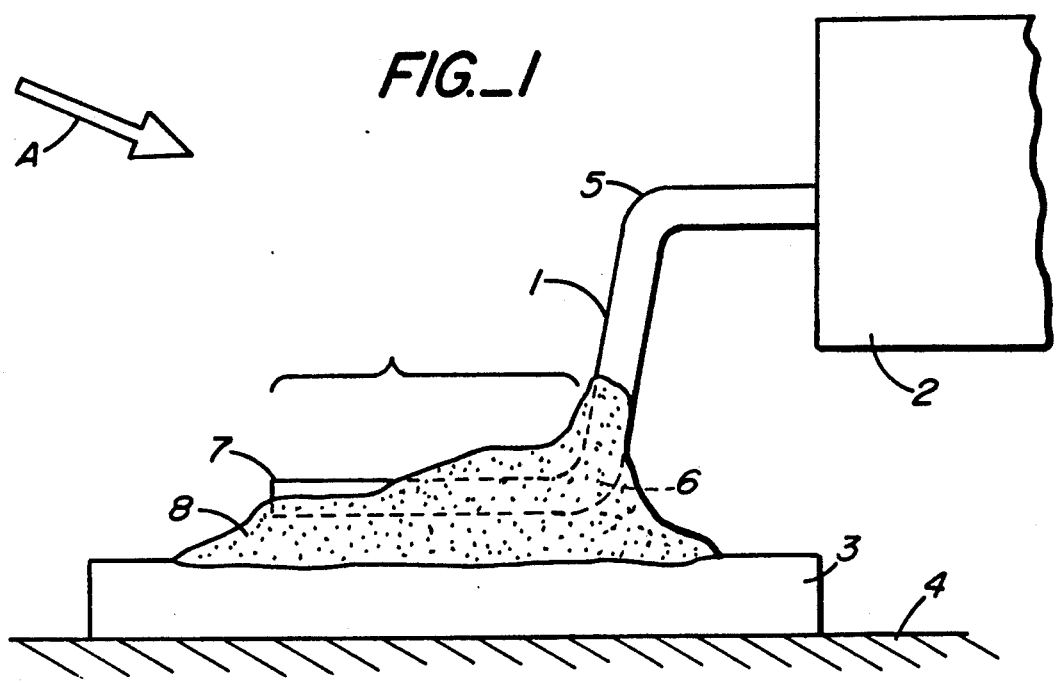
FIG._1
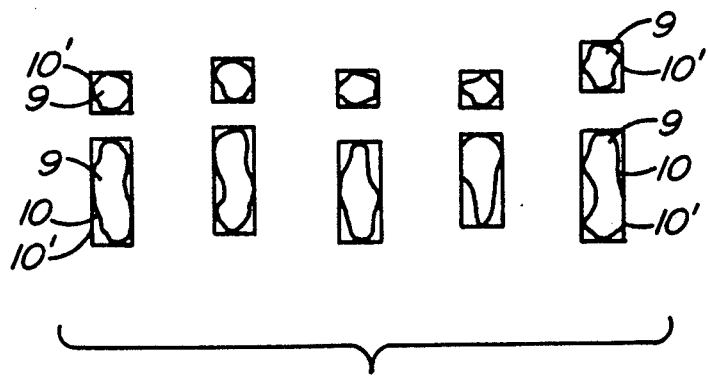
FIG._2
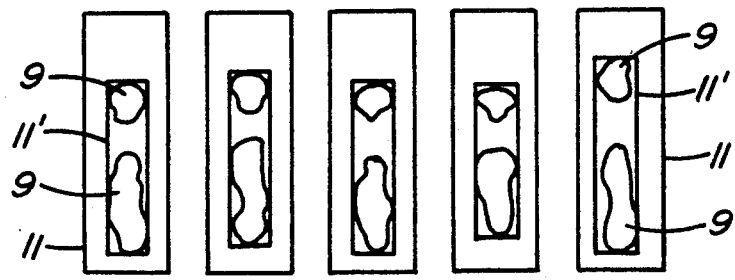
FIG._3

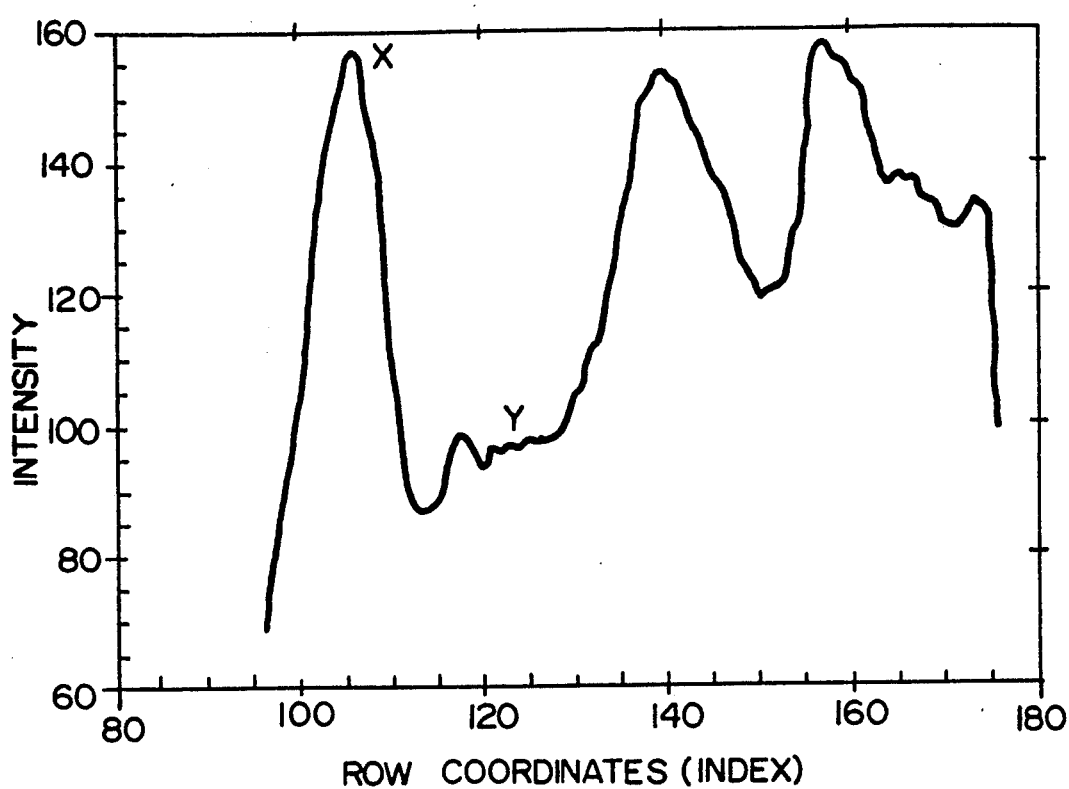
FIG._4
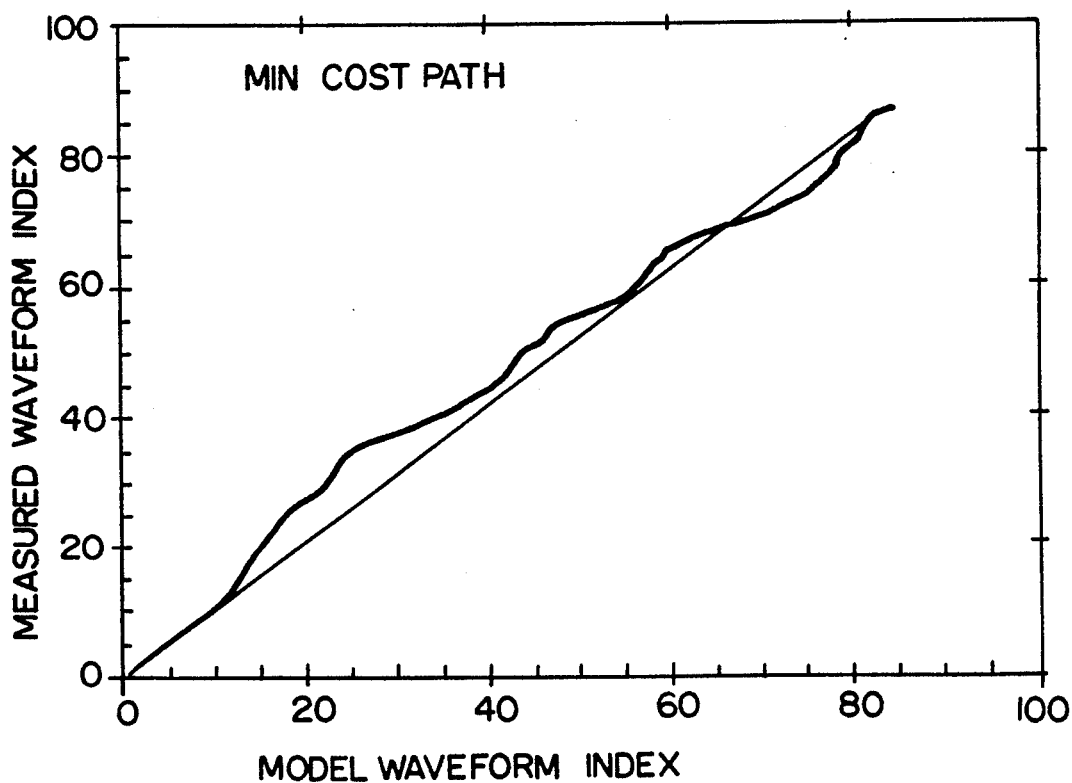
FIG._6

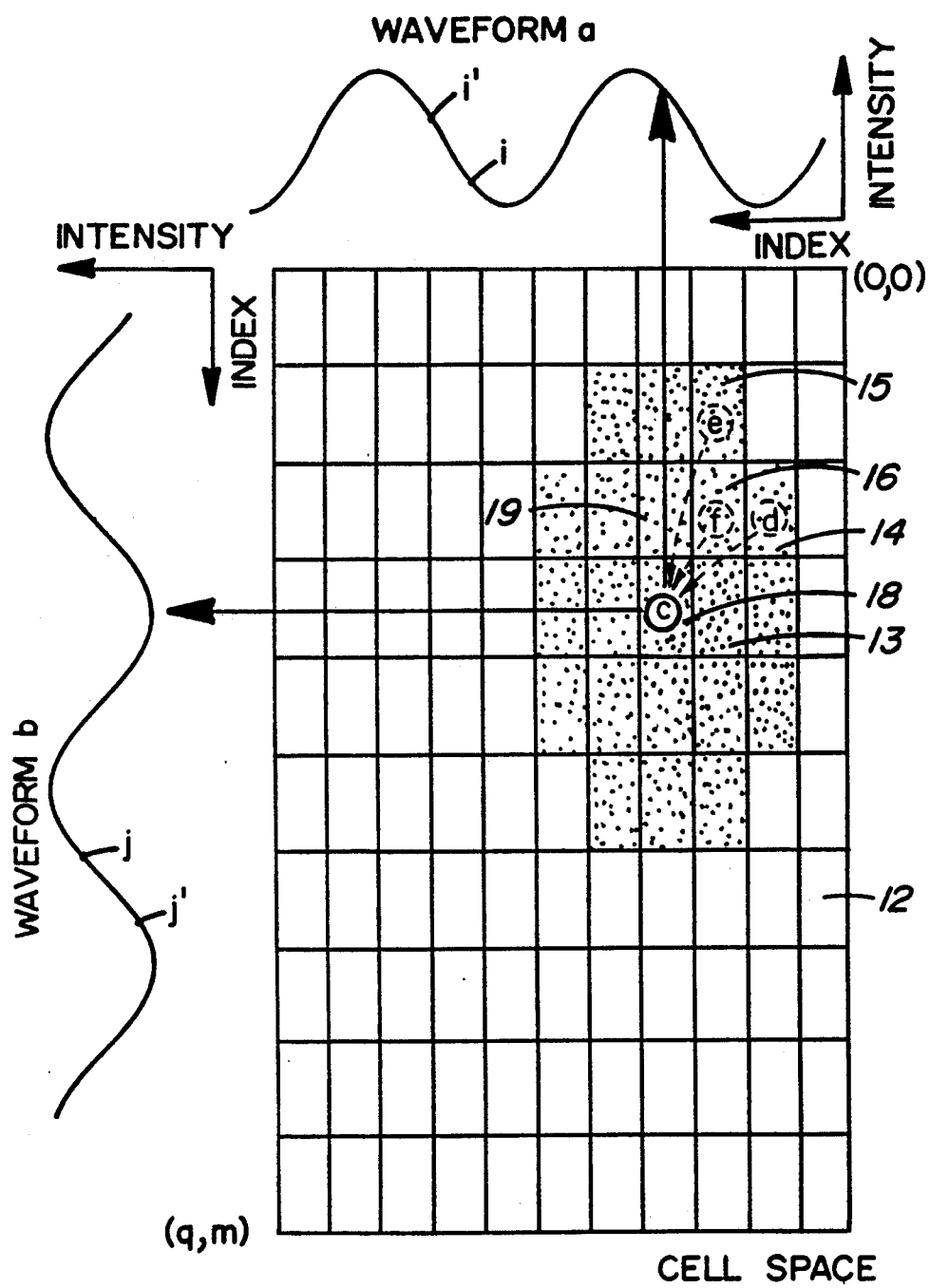
FIG._5

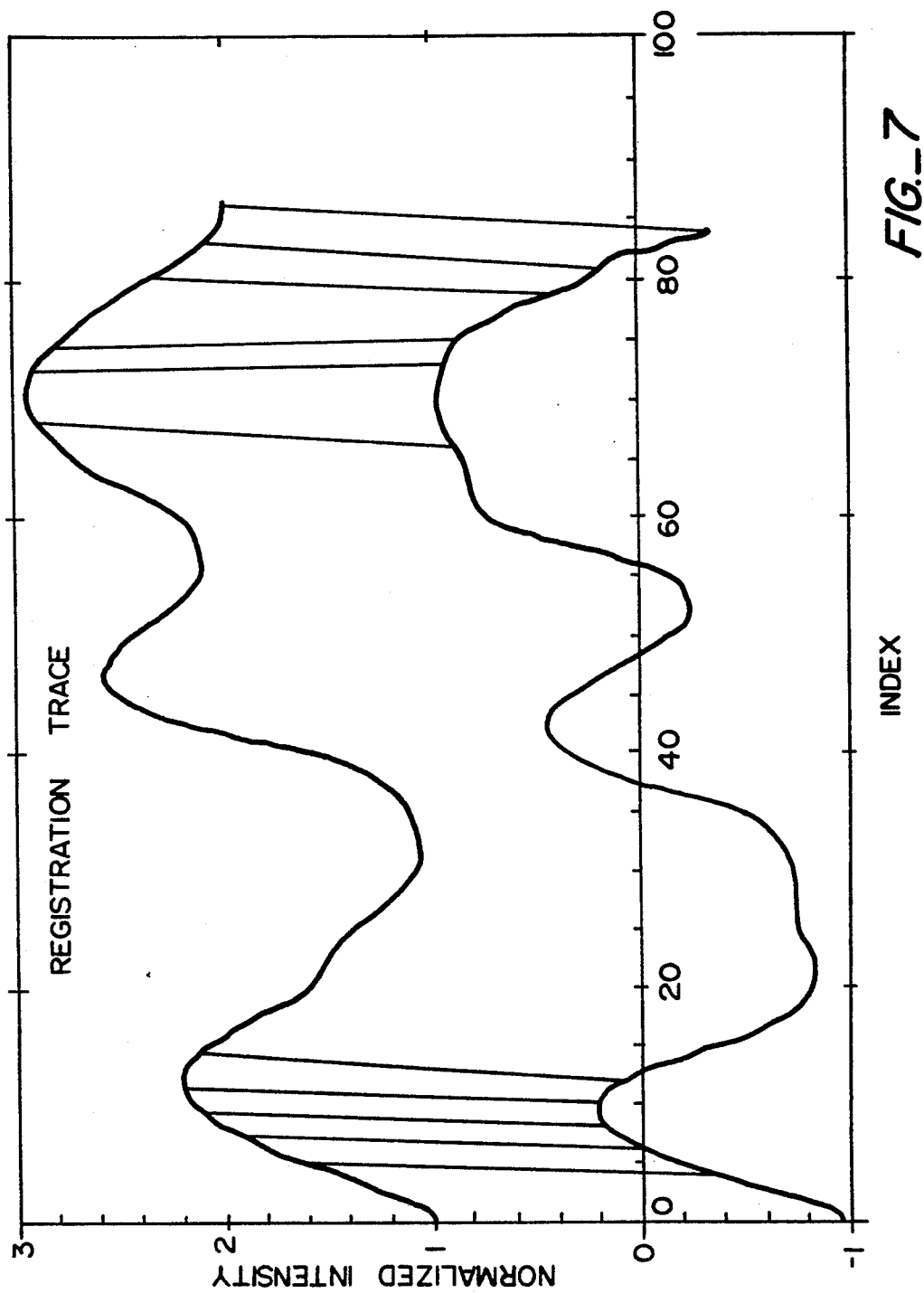
FIG._7

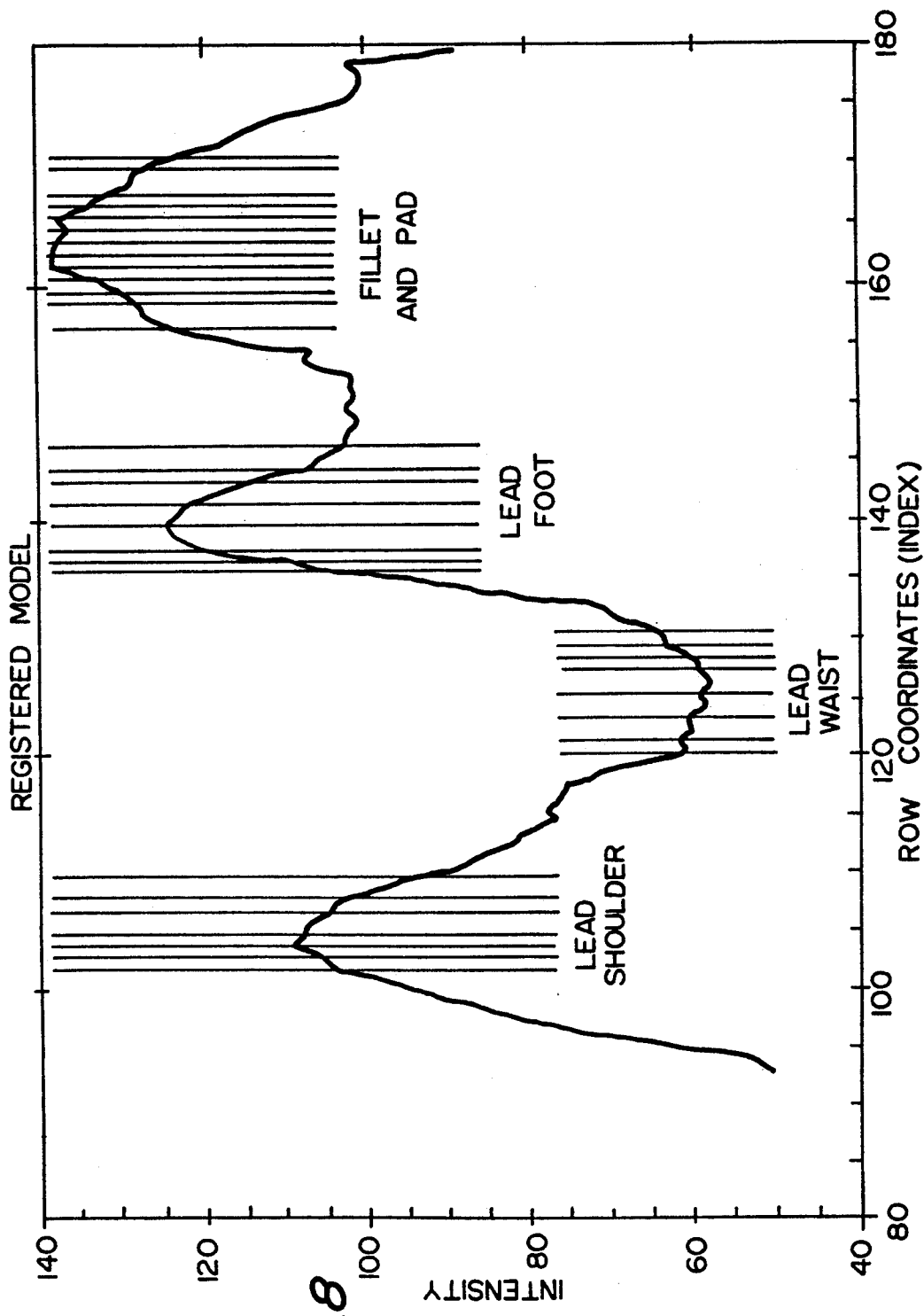
FIG._8

METHOD FOR INSPECTING THE LEADS OF ELECTRICAL COMPONENTS ON SURFACE MOUNT PRINTED CIRCUIT BOARDS

BACKGROUND OF THE INVENTION

1. Field of the Invention

The present invention generally relates to systems for inspecting curved surfaces and, more particularly, to systems that inspect curved surfaces such as the ones formed by solder joints that connect electronic components of the surface mount type to circuit boards.

2. State of the Art

For assemblies employing integrated circuit packages, circuit malfunctions are often traceable to faulty solder connections between a board and the leads of a circuit package mounted on the board. This is especially true for circuit packages of the surface-mount type, since those packages have leads which are usually finer and more closely spaced and, hence, more difficult to solder correctly than leads on circuit packages of the dual in-line pin (DIP) type. Circuit packages of the surface-mount type are designed, as their name implies, for electrical connection to the surface of a circuit board. The leads of surface-mounted packages can have various shapes including "J" and gull-wing like shapes.

For mounting circuit packages of the surface-mount type to a circuit board, solder paste is placed onto minute solder pads that are precisely located on the board to match the pattern, or "footprint", of properly aligned leads on each circuit package. After the desired number of circuit packages are placed on the board with the leads of the packages embedded in the solder paste on the pads, the packages are permanently soldered into place. To achieve satisfactory electrical connections, each of the solder joints must be adequately completed.

To assure that solder joints adequately connect surface-mount circuit packages to printed circuit boards, inspection is required. Although inspection can be done manually, such techniques are time-consuming and tedious. Accordingly, efforts have been made to automate the inspection task. However, automated inspection of solder joints is quite difficult because of the variability in appearance of acceptable solder joints, because of the highly specular nature of solder surfaces, and because of the three-dimensional nature of solder surfaces.

One suggested system for automated inspection of solder joints at the leads of surface-mounted circuit packages is set forth in U.S. Pat. No. 4,668,939. Specifically, that patent discloses an automated inspection system which inspects solder bumps on chip carriers by using video cameras, i.e., cameras that depict a scene in two dimensions. According to the patent, images provided by the video camera are processed to provide one-dimensional intensity plots which can be analyzed to detect missing, bridged or excessive solder bumps.

SUMMARY OF THE INVENTION

Generally speaking, the present invention provides a method for inspecting solder joints that are formed between surface mount electronic components and printed circuit boards. In addition, the present invention provides methods for determining the type of faults that are associated with faulty ones of such joints.

Preferably, the method of the present invention includes the steps of: obtaining an image of a plurality of the leads of the electronic component; for each obtained image, representing segments of the image that correspond to each of the leads by polygons; projecting pixel intensity values within each polygon each onto an axial dimension to provide a measured waveform; comparing the measured waveform for each lead with a corresponding model waveform; and, classifying each lead as being either satisfactory or unsatisfactory on the basis of said comparisons.

The step of comparing a measured waveform with a corresponding model waveform preferably is accomplished by dynamic programming, whereby data points of the measured waveform are placed into correspondence with data points of a model waveform to provide a cost value which indicates the "goodness of fit". During the classification of leads, the cost value, together with the length of the measured projection of a lead bounding box, is used to immediately discriminate "good", or satisfactory leads from "bad", or unsatisfactory leads in accordance with statistical pattern classification schemes.

Also, the measured waveforms can be structurally analyzed to determine the nature of faults associated with unsatisfactory leads. Structural analysis can be performed by checking whether various properties of a model waveform are met by different sections of a measured waveform The sections can be indicated on the model waveform and deducing the corresponding sections on the measured waveform using the aforementioned matching technique.

BRIEF DESCRIPTION OF THE DRAWINGS

The present invention can be further understood by reference to the following description and appended drawings which illustrate the preferred embodiments of the invention. For purposes of clarity, identical parts are given the same reference numbers in the various drawing figures. In the drawings:

FIG. 1 is a schematic drawing of a gull-wing lead;

FIG. 2 is an image of a plurality of gull-wing leads, as viewed from the angle A shown in FIG. 1, which image has been operated upon in accordance with the preferred embodiment of the present invention to provide lead bounding boxes;

FIG. 3 shows is an image of leads similar to FIG. 2, which image has been further operated upon in accordance with the preferred embodiment of the present invention;

FIG. 4 shows a waveform which results from the rectilinear projection of a lead bounding box such as the one shown in FIG. 2, with the row coordinates for the lead bounding box image being plotted on the abscissa and the average intensity of the pixels in each row in the lead bounding box being plotted along the ordinate;

FIG. 5 shows a cell space for registering two waveforms resulting from rectilinear projections of two different lead bounding boxes;

FIG. 6 shows a typical minimum cost path through the cell space of FIG. 5;

FIG. 7 shows two waveforms that are in registration with one another; and

FIG. 8 shows an exemplary model waveform for gull-wing leads, which waveform has been divided up into four sections for purposes of inspection.

DETAILED DESCRIPTION OF THE PREFERRED EMBODIMENTS

FIG. 1 shows a gull-wing lead 1 that connects a surface mount electronic component 2 to a solder pad 3 of a printed circuit board 4. The gull-wing lead includes a shoulder 5 which constitutes a first bend in the lead, and a heel 6 which constitutes a second bend in the lead. The section of the lead between the shoulder and the heel constitutes the lead's waist. The distal end of the lead is referred to as the lead's toe and is designated by numeral 7. The section of the lead between heel 6 and toe 7 is referred to as the lead's foot, and is connected to pad 3 by a solder fillet or joint 8.

Methods will now be described for inspecting solder joints such as the one shown in FIG. 1 to detect the quality of the joints and, thus, the quality of the connections between electronic components and printed circuit boards.

As a first step in the inspection method, images of surface mount components on a printed circuit board are obtained by illuminating the board with highly diffuse light. Then, each image is "segmented" to isolate the leads and to permit analysis of the solder joints at the individual leads. An example of an image of a group of gull-wing leads is shown in FIG. 2.

In practice, intensity thresholds are computed for images that are to be segmented. The intensity thresholds can be automatically computed using, for example, standard methods such as described in "A threshold selection method from gray-level histograms", N. Otsu, IEEE Transaction on Systems, Man, and Cybernetics, 9, 1, January 1979, pp. 62–66. The intensity thresholds are used for partitioning each image into two kinds of regions: "subject" regions where the intensity values of the pixels in the region are above the intensity threshold, and "background" regions where the intensity values of the pixels are below the threshold. In FIG. 2, subject regions are designated by the number 9.

After images of the leads of surface mount components are partitioned, the subject regions are chain encoded. As a result of chain encoding, the boundaries of subject regions are represented as chains of arcs that connect pixels located on the boundary of the regions. Chain encoding can be accomplished, for example, with the methods described in Freeman, Herbert; "Computer Processing of Line-Drawing Images", *Computing Surveys* Vol. 6, No. 1, March 1974. In FIG. 2, the chain encoded boundaries of subject regions are designated by the number 10.

After subject regions are chain encoded, a bounding polygon or "box" is computed for each of the chain encoded regions. Preferably, the chosen bounding boxes are the minimum area rectangles whose sides parallel the image's coordinate axes. Minimum area rectangles can be constructed by computing the minimum and the maximum row and column values of the pixels that form the chain of arcs. In FIG. 2, the minimum area rectangles for the chain encoded regions are designated by the number 10'.

After minimum area bounding boxes have been computed for each chain encoded subject region, polygonal areas can be computed that represent the expected location for each solder joint. Modeling of expected locations can facilitate with conventional computer aided design (CAD) databases for the particular printed circuit board being analyzed. Preferably, the computed polygonal areas are rectangular. In FIG. 3, the expected rectangular areas for the leads of FIG. 2 are identified by the numbers 11.

In practice, the expected locations are used to form clusters of bounding boxes into regions representing leads. An algorithm for clustering the minimum area bounding boxes can be generally as follows:

a) compare the minimum area bounding box for each image of a lead with all of the expected locations;

b) for those minimum area bounding boxes that intersect or overlap an expected location, designate those bounding boxes as being part of the lead associated with that expected location;

c) if a minimum area bounding box intersects more than one expected location, add the minimum area bounding box to the set representing each of the intersected expected locations;

d) reject the remaining minimum area bounding boxes;

e) for each accepted bounding boxes and each expected location, calculate a lead bounding box that represents the sum of the minimum area bounding boxes included in each of the sets. An example of a set of minimum area bounding boxes constituting a lead is indicated by element 11' in FIG. 3.

After bounding boxes are clustered as described above, several properties of imaged leads may be conveniently determined. For example, a determination can be made that a lead is missing from an expected location. (This conclusion would follow from the fact that an expected location is not intersected by any of the minimum area bounding boxes.) Also a determination can be made that lead components are missing if the lead bounding box associated with an expected location for a lead is smaller than expected. As another example, a solder bridge between leads can be detected if two adjacent lead bounding boxes intersect one another or are identical.

After lead bounding boxes are computed as described above, gray level intensities associated with each of the lead bounding boxes are rectilinearly projected onto the axes parallel to the axes of the lead images. In practice, the rectilinear projections are accomplished by calculating the average intensity value of each pixel row (or column) inside of a lead bounding box. For example, if a lead happens to be vertically aligned in an image, the projected waveform consists of the average intensitY value of each pixel row in the image, indexed by the vertical coordinates of the row. FIG. 4 shows an example of a waveform that results from the rectilinear projection of a vertically aligned lead image.

In practice, it is preferred that the rectilinearly projected waveforms are normalized. Normalization can be accomplished, for instance, by using an averaging filter to convolve the waveform for each projected lead bounding box. After normalization, it is convenient to map the intensity range of the normalized waveform so that the average intensity is equal to zero and the maximum absolute intensity is equal to +1.

After the rectilinear projections have been produced, the projected waveforms are registered, or matched. Preferably, registration is accomplished by a technique known as dynamic warping.

The purpose of employing dynamic warping to register pairs of discrete waveforms is to provide a list of corresponding points in pairs of waveforms. Registration between two waveforms 15 may be expressed by a couplet of numbers (i,j). For example, the couplet (i,j) means that a first waveform at an index coordinate point, or index i is registered with a second waveform at an index coordinate point j. It may be appreciated that the set of all couplets that indicate corresponding points between two waveforms can be mapped in a two dimensional table, or cell space, such as designated by the number 12 in FIG. 5.

Generally speaking, two waveforms are in registration if a list of corresponding points in the waveforms is both continuous and monotonic. The continuity constraint can be satisfied by requiring the registration to be a continuous path through the cell space table. The monotonicity constraint can be satisfied if each waveform is ordered by its indexes and the ordering is preserved. For example, i' is greater than i for the waveform "a" in FIG. 5, i matches j of the waveform "b", and i' matches j' of the waveform "b", and, therefore, j is less than j' for the waveform "b". In other words, by requiring the registration of the two waveforms to constitute a monotonic path through the table such that (i, j) is a first point of correspondence in a list and (i', j') is the next point of correspondence in the list, then i is less than i' and j is less than j'. In table 12 in FIG. 5, cell 13 represents a point of correspondence between an indexed coordinate point in each of two waveforms "a" and "b", respectively.

After pairs of waveforms are registered by dynamic warping or a similar technique, measured waveforms for each lead bounding box can be compared with a corresponding model waveform, or "golden waveform" In the present context, a golden waveform is a model waveform that has been preconstructed for each type of lead and pad combination which will be encountered during an analysis, or inspection, of the joints of a printed circuit board on which all of the solder connections are satisfactory. In other words, a golden waveform is a model waveform for a corresponding type of electronic component lead and represents the ideal waveform.

In typical practice, one golden waveform is selected for each type of electronic component. By comparing a measured waveform for a lead bounding box with a corresponding golden waveform, the resulting match of the indexed points on the measured waveform relative to the golden waveform indicates the "goodness of fit". For example, the waveform "a" described above with respect to FIG. 5 could be a golden waveform for a particular type of electronic component lead, and the waveform "b" could be a measured waveform corresponding to the image of a lead bounding box under inspection.

More particularly, by comparing a measured waveform with a corresponding golden waveform, the solder connections of inspected leads can be automatically classified as being either good (i.e., satisfactory) or bad (i.e., unsatisfactory) on the basis of the particular value of a "cost function." The particular value of the cost function represents the "cost" a path through a cell space table such as shown in FIG. 5. As will be described below, the path that represents the best matching of a pair of waveforms is the path with the lowest cost.

A cost function that is effective for automatically inspecting gull-wing leads on surfacemount electronic components will now be described. In constructing the cost function, the path through a cell space table is considered as consisting of a starting node (0, 0) followed by a list of arcs. Each arc represents the vector difference between two nodes plus the node on which the arc terminates. The cost of an arc is defined as the length of the arc times the cost of an associated node. The cost of a node is the absolute value of the difference of the values of the waveforms at the points of correspondence. Thus, the cost of a path is the sum of the cost of the arcs that constitute the path.

By way of example, assume that waveform "a" is to be registered with waveform "b" in FIG. 5. Waveform "a" can be represented as a set of indexed points $a_i$, where i is greater than or equal to 1 and less than or equal to q. Likewise, waveform "b" can be represented as the set of indexed points $b_j$, where j is greater than or equal to 1 and less than or equal to m. Then, the list of nodes in a path through the two-dimensional table 12 is represented as the set of correspondence points $n_k$, where $n_k$ equals $(a_{ik}, b_{jk})$ and k is greater than or equal to 1 and less than or equal to n. The total cost of the path can be expressed as:

$$\text{cost}(p) = \sum_{k=2}^{n} |n_k - n_{k-1}| |a_{ik} - b_{jk}|$$

In practice, the minimum cost path through a cell space can be calculated recursively by using dynamic programming. For example, let C (i, j) be the cost of the minimum cost path from a cell (0, 0) to a cell (i, j). The possible arcs from one cell to the next are represented by a set designated "arcs", wherein:
arcs = [(1,1),(1,2),(2,1)]

In accordance with the dynamic programming technique then, for C(0,0) = 0, $$C(i,j) = C((i,j) - \text{arc}) + |\text{arc}| * |a_i - b_j|$$

where "arc" in the foregoing equation is selected from the previously mentioned set designated "arcs" such that C(i,j) is minimized. It should be noted that the cost of any cell which has no predecessors in the cell space is considered infinite.

The cost of the minimum cost path is then given by C(q,m). The dynamic programming thus makes use of a two-dimensional array having the dimensions q x m. The value of every cell in the array is calculated, beginning at (0, 0) and progressing along a path of the cell space in such a way that, when calculating any cell, the predecessor cells, if they exist, are already computed. The arc is stored for each cell and a minimum cost path is reconstructed by simply following the arcs back from the cell (q,m) to the cell (0, 0). A typical minimum cost path is shown in FIG. 6.

Further with regard to FIG. 6, it may be noted that the cost of matching a model waveform with itself is zero. This situation is depicted by the straight line shown in FIG. 6.

An example of a pair of matched (i.e., registered) waveforms is shown in FIG. 7. In that drawing, the measured waveform has been raised to make the registration, or matching, appear more clearly. The vertical lines between the two waveforms indicate that those indexed points on the two waveforms correspond to one another.

The cost values that are calculated while registering a measured waveform with a model waveform can be subsequently used as a feature in a statistical classifier. In practice, the statistical classifier representing a preferred statistical pattern classification scheme for inspecting leads of surface mount components.

For such statistical pattern classification, the leads in a statistically significant sample are first classified by manual techniques as being either good, bad, or questionable. The leads from this statistically significant sample are then matched with a model and the matching costs are calculated as described above are plotted. A matching cost threshold is then calculated from the plot.

After a threshold has been calculated for classifying the quality of the measured waveforms associated with the statistically significant sample, leads of unknown quality can be inspected and classified automatically by matching the waveforms of the bounding boxes of the newly inspected leads with the model waveform as described previously. Then, all of the newly inspected leads with a matching cost below the threshold calculated for the statistically significant sample can be considered to be good and all leads with a matching cost above the threshold are considered to be bad. In practice, a pair of thresholds can also be established for the statistically significant sample to discriminate questionable cases; i.e., leads which do not clearly fall into a classification as being good or bad.

Leads that have been judged to be bad or questionable can then be analyzed to determine the nature of their defects. During the analysis, questionable leads may be "cleared"; i.e., determined to be satisfactory. This analysis is referred to as "structural analysis" in the following.

In the structural analysis process, faults in bad leads can be identified by checking whether various properties of the leads are met by different sections of the measured waveform. Generally speaking, this is accomplished by specifying the sections on a golden waveform and, then, deducing the corresponding sections on the measured waveform using the registration techniques described above.

In practice, the discrimination of leads in the manner described above can be plotted with other features of the leads which have been inspected. Such presentation of data will be described more specifically below. It should further be noted that unsupervised learning, in which no threshold is needed for discrimination of leads, may also be used. Unsupervised learning is generally described, for example, in "Pattern Classification and Scene Analysis", R. Duda and P. Hart, John Wiley & Sons, 1973.

A description of a structural analysis method will now be provided. To perform structural analysis for the purpose of judging the fault in a lead which has been determined to be bad or questionable, a model of the lead (i.e., a golden waveform) is treated as a data structure describing the ideal waveform for a corresponding type of electronic component and properties of its values. In particular, each model contains:

The name of the model;

The number n of coordinate pairs in the waveform, each coordinate pair of the model waveform being identified by an indexed point, or index, along the waveform and by a corresponding intensity value, or a value;

A list of the n pairs (by index and corresponding value (i.e., [index, value]) constituting the waveform;

A list of n tests, (i.e., one test for each of the n pairs) with which to evaluate the model waveform;

A list of n factors to be multiplied with each measured value before conducting the relevant test for the type of lead currently being inspected; and, A list of n reports. (For example, a report is produced for a measured value if the measured value failed the relevant test).

Models may be read from and written to files, they may be tested with respect to the measured data derived from a measured waveform, and they may be depicted graphically, again with respect to measured data.

Once a measured waveform has been registered with a model waveform, tests can be made involving a pointwise comparison of measured data (associated with a measured waveform) with model data (associated with a model waveform). For example, the following process can be used for gull-wing leads. Let $[Y_{min}, Y_{min}+\text{range}]$ describe a y interval that the intensity of the model waveform falls within. Recall that measured waveforms were normalized in the preferred embodiment as described above such that $y_{min}$ is greater than or equal to negative one and less than or equal to zero, and that the range of the intensity values is greater than or equal to one and less than or equal to two, as shown for example, in FIG. 7.

Thus, for each data point three very simple tests are useful for the purpose of analyzing the nature of a bad or questionable gull-wing lead. More specifically, a first test is useful to determine whether a data point of the measured waveform fits within the intensity range of the model waveform. In this regard, it should be noted that a data point determined to be in correspondence with a point on the model waveform always passes this test. If, however, no points of correspondence between the measured waveform and the model waveform exist, a null condition is determined to exist.

A second test is useful to determine that the intensity value of a measured waveform falls within the upper portion of the range as determined by the intensity factor, or factors, which was associated with the data point. This association of an intensity factor with the data point is determined by the registration, or matching, of the measured waveform with the model waveform as described above.

A third test that is useful in analyzing the nature of a bad or questionable lead involves determining that a measured intensity value of the measured waveform falls within the lower portion of the range as determined by the factor associated with the data point. Again, this association of an intensity factor with a data point is determined by the registration, or matching, of the two waveforms as described previously.

For present purposes, registration of a measured waveform with a model waveform can also be referred to as a trace. A graphic illustration of a model which can be used to identify the nature of a bad or questionable lead in accordance with a preferred embodiment of the present invention is shown in FIG. 8. As can be seen from this figure, gull-wing leads are divided into four sections, each of which is separately analyzed during the structural analysis. Thus, each section has its own test, intensity factor and report included with the model waveform. That is, every data point of a measured waveform determined to correspond to a model point in a given section of the model waveform will be tested and reported in the same way. For gull-wing leads, the intent is to insure that there is sufficient solder at the joint and to further insure that no solder has wicked up to the waist or shoulder of the lead.

A discussion will now be provided of a manner in which the matching cost associated with a particular measured waveform can be combined with other features to provide a more valuable presentation of information regarding the quality of joints inspected on a printed circuit board.

For example, information regarding the matching cost of each of a plurality of joints can be plotted against an index which merely represents the number of each lead which has been inspected. That is, the lead index number is merely an arbitrary identifier which could appear on the abscissa of a plot, with the matching cost of each indexed lead appearing on the ordinate. Because the lead index number is an arbitrary identifier which provides no significant additional information, such a scatter plot merely represents a one-dimensional feature space.

A linear discriminate which could be used to enhance the presentation of data and the statistical classification of the leads would be a scalar matching cost threshold. A scatter plot with such a two-dimensional feature space could, for example, be constructed with the matching cost of each lead being plotted against profile size. The profile size is merely the ratio of the number of sample points in the measured waveform with the number of sample points in the model waveform. Such a scatter plot provides improved discrimination and multiple categories. A linear discriminate in this case would be a straight line in the space.

In presenting the data in a two-dimensional feature space, various accommodations can be made for characteristics which may influence the inspection of the leads. For example, certain detected waveforms might not be matchable, such as shadowed leads which can give very short waveforms. Accordingly, these matches can arbitrarily be given a cost of one for purposes of the aforementioned statistical analysis using a two-dimensional feature space.

Thus, the method as described above provides the ability to determine the type of error in two separate ways: by classification in a multidimensional feature space and by examination via structural analysis of the lead's projected intensity waveform to determine the nature of the problem with the joint. Faults which may be detected in this way include missing solder, solder wicking, excess solder and improperly distributed solder.

Using the statistical classification schemes, an incorrectly classified good lead can be detected. For example, a misplaced good lead could result from the segmentation process described above. More specifically, a printed trace could, for example, appear under a lead in the image of the lead. This trace is bright enough to be picked up by the automatic threshold, narrow enough not to be rejected by the clustering process, and coincidentally also falls within the expected region for this lead. For this reason, this lower trace would be included with the rest of the lead such that a rather unusual projected waveform results for the lead. However, using the statistical classification scheme as described above, it can immediately be determined that the classification of this lead's matching cost was misplaced. Furthermore, because the measured waveform associated with this lead is longer than it should be, a greater number of measured data points are associated with the projected waveform such that a high profile size results. Thus, the matching cost for this lead can be determined to have been improperly plotted.

The foregoing has described the principles, preferred embodiments and modes of operation of the present invention. However, the present invention should not be construed as being limited to the particular embodiments discussed. For example, although specific reference has been made to gull-wing leads for connecting surface mounted electronic components onto printed circuit boards by soldering, the described methods can be utilized with other types of connections, leads, and/or joints. Accordingly, the above-described embodiments should be regarded as illustrative rather than restrictive, and it should be appreciated that workers skilled in the art may make variations in those embodiments without departing from the spirit or scope of the present invention as defined by the following claims.

What is claimed:

1. A method for inspecting a joint used to connect leads of a surface mount electronic component onto a pad of a printed circuit board, comprising the steps of:

taking an image of the leads;

chain encoding regions of the image which have intensity values above a predetermined intensity threshold;

computing minimum area bounding boxes for each of the chain encoded regions;

modeling an expected region for each lead and pad combination;

determining those chain encoded bounding boxes which intersect each expected region;

computing a lead bounding box for each lead on the basis of the chain encoded bounding boxes to form a segmented image of the leads;

testing the segmented image consisting of the lead bounding boxes for missing leads and lead bridges;

projecting each lead bounding box as a measured waveform onto an axial dimension of the lead's bounding box;

comparing the measured waveform for each lead with a corresponding model waveform to enable inspection; and, classifying each lead as being either satisfactory or unsatisfactory on the basis of said comparison.

2. A method for inspecting joints such as the joints between a printed circuit board and a surface-mount electronic component placed onto the board, comprising the steps of:

obtaining image of a plurality of the leads of the electronic component;

for each obtained image, representing segments of the image that correspond to each of the leads by polygons;

projecting pixel intensity values within each polygon each onto an axial dimension to provide a measured waveform;

comparing the measured waveform for each lead with a corresponding model waveform by placing points of each measured waveform into correspondence with data points of the model waveform to return a cost value which indicates goodness of fit;

classifying each lead as being either satisfactory or unsatisfactory by determining the length of the measured projection of a lead bonding box; and, using the cost value and the length of the measured projection to discriminate good leads from bad leads.

3. A method for inspecting joints such as the joints between a printed circuit board and a surface-mount electronic component placed onto the board, comprising the steps of:

obtaining an image of a plurality of the leads of the electronic component;

for each obtained image, representing segments of the image that correspond to each of the leads by polygons;

projecting pixel intensity values within each polygon each onto an axial dimension to provide a measured waveform;

comparing the measured waveform for each lead with a corresponding model waveform; and, classifying each lead as being either satisfactory or unsatisfactory by determining a matching cost threshold from a statistically significant sample of leads.

4. The method of claim 3, wherein said step of determining a matching cost threshold further includes:

determining a pair of thresholds for discriminating questionable leads which cannot be immediately classified as either good or bad.

5. A method for inspecting joints such as the joints between a printed circuit board and a surface-mount electronic component placed onto the board, comprising the steps of:

obtaining an image of a plurality of the leads of the electronic component;

for each obtained image, representing segments of the image that correspond to each of the leads by polygons;

projecting pixel intensity values within each polygon each onto an axial dimension to provide a measured waveform;

comparing the measured waveform for each lead with a corresponding model waveform by placing points of each measured waveform into correspondence with data points of the model waveform to return a cost value which indicates goodness of fit;

classifying each lead as being either satisfactory or unsatisfactory on the basis of said comparisons; and, testing the segmented images for missing leads and solder bridges by clustering bounding boxes into expected locations representing leads as follows:

a) comparing a minimum area bounding box for each image of a lead with all of the expected locations;

b) for those minimum area bounding boxes that intersect or overlap an expected location, designating those bounding boxes as being part of the lead associated with that expected location;

c) if a minimum area bounding box intersects more than one expected location, adding the minimum area bounding box to the set representing each of the intersected expected locations;

d) rejecting the remaining minimum area bounding boxes and;

e) for each accepted bounding box and each expected location, calculating a lead bounding box that represents the sum of the minimum area bounding boxes included in each of the sets.

* * * * *